United States Patent [19]
Dobson

[11] Patent Number: 4,666,565
[45] Date of Patent: May 19, 1987

[54] GAS SENSOR AND METHOD
[75] Inventor: John V. Dobson, Hartlepool, England
[73] Assignee: British Gas Corporation, London, England
[21] Appl. No.: 884,882
[22] Filed: Jul. 10, 1986

Related U.S. Application Data

[63] Continuation of Ser. No. 814,168, Dec. 23, 1985, abandoned, which is a continuation of Ser. No. 724,037, Apr. 17, 1985, abandoned, which is a continuation of Ser. No. 603,933, Apr. 26, 1984, abandoned.

[30] Foreign Application Priority Data

Apr. 28, 1983 [GB] United Kingdom ............... 8311552

[51] Int. Cl.⁴ ........................................... G01N 27/52
[52] U.S. Cl. .................................. 204/1 T; 204/412; 204/431; 204/432
[58] Field of Search ............... 204/412, 431, 432, 1 N, 204/1 K, 1 F

[56] References Cited

U.S. PATENT DOCUMENTS 3,755,125  8/1973  Shaw et al. .................... 204/415 X
4,394,239  7/1983  Kitzelmann et al. ............. 204/414
4,406,770  9/1983  Chan et al. ...................... 204/406

FOREIGN PATENT DOCUMENTS 1372245   10/1974  United Kingdom ............... 204/431
1433071    4/1976  United Kingdom ............... 204/431
1473250    5/1977  United Kingdom ............... 204/431
1484886    9/1977  United Kingdom ............... 204/431
2075197A  11/1981  United Kingdom ............... 204/431
2094005A   9/1982  United Kingdom ............... 204/431

Primary Examiner—G. L. Kaplan
Attorney, Agent, or Firm—Larson and Taylor

[57] ABSTRACT

An electrochemical cell for use in the detection and measurement of water soluble gases includes a vessel having a first chamber adapted to receive and contain said gas and having located therein a working electrode and a second chamber adapted to contain an electrolyte and having located therein a reference electrode arranged to be in contact with said electrolyte. A counter electrode is located in either the first or second chamber. The working electrode consists of an absorbent material communicating between said first and second chambers, which is adapted to be in contact with said electrolyte and has an electro-active substrate deposited on at least a portion of the surface of that part of the material located in the first chamber.

3 Claims, 7 Drawing Figures

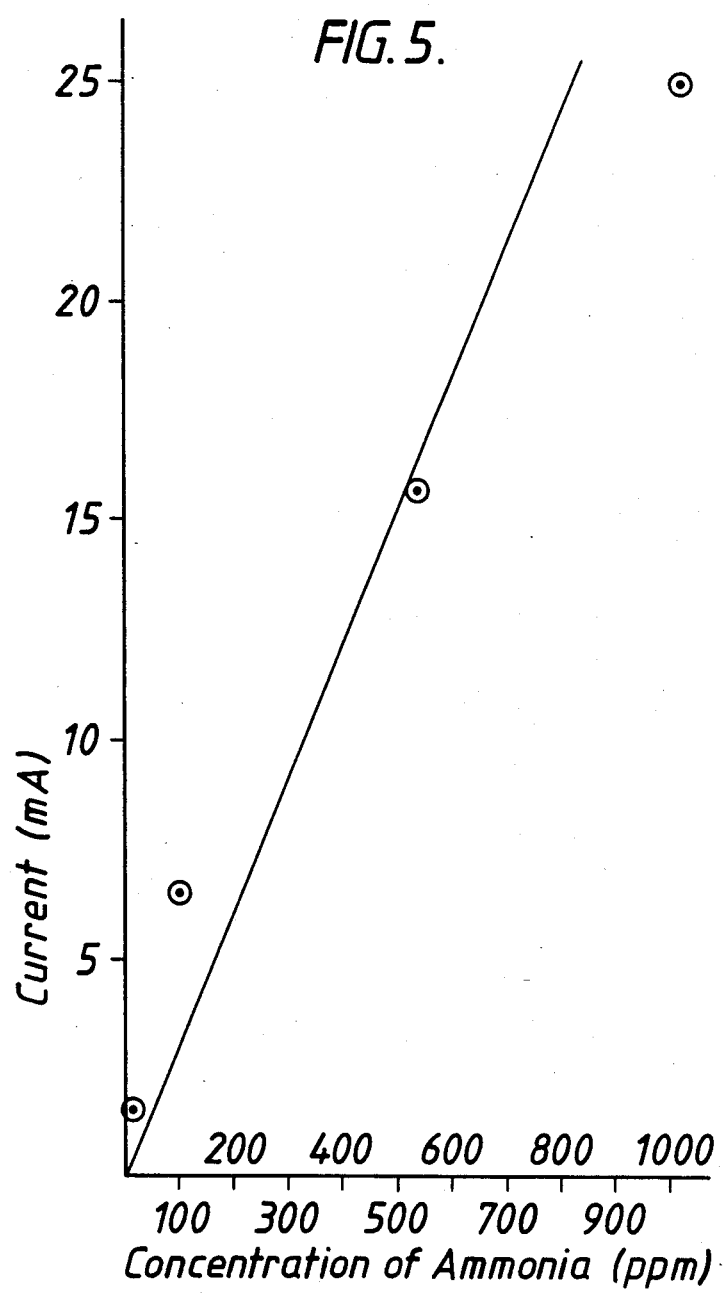

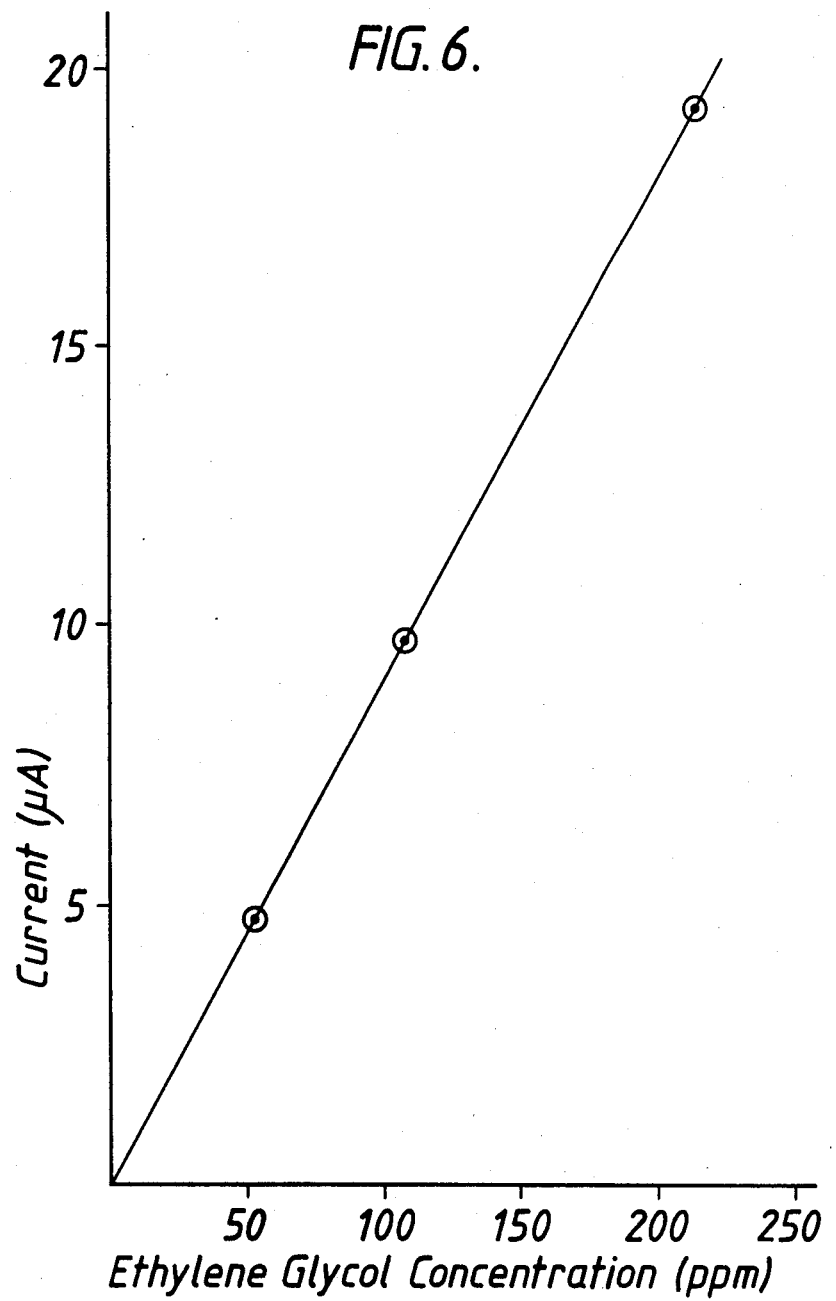

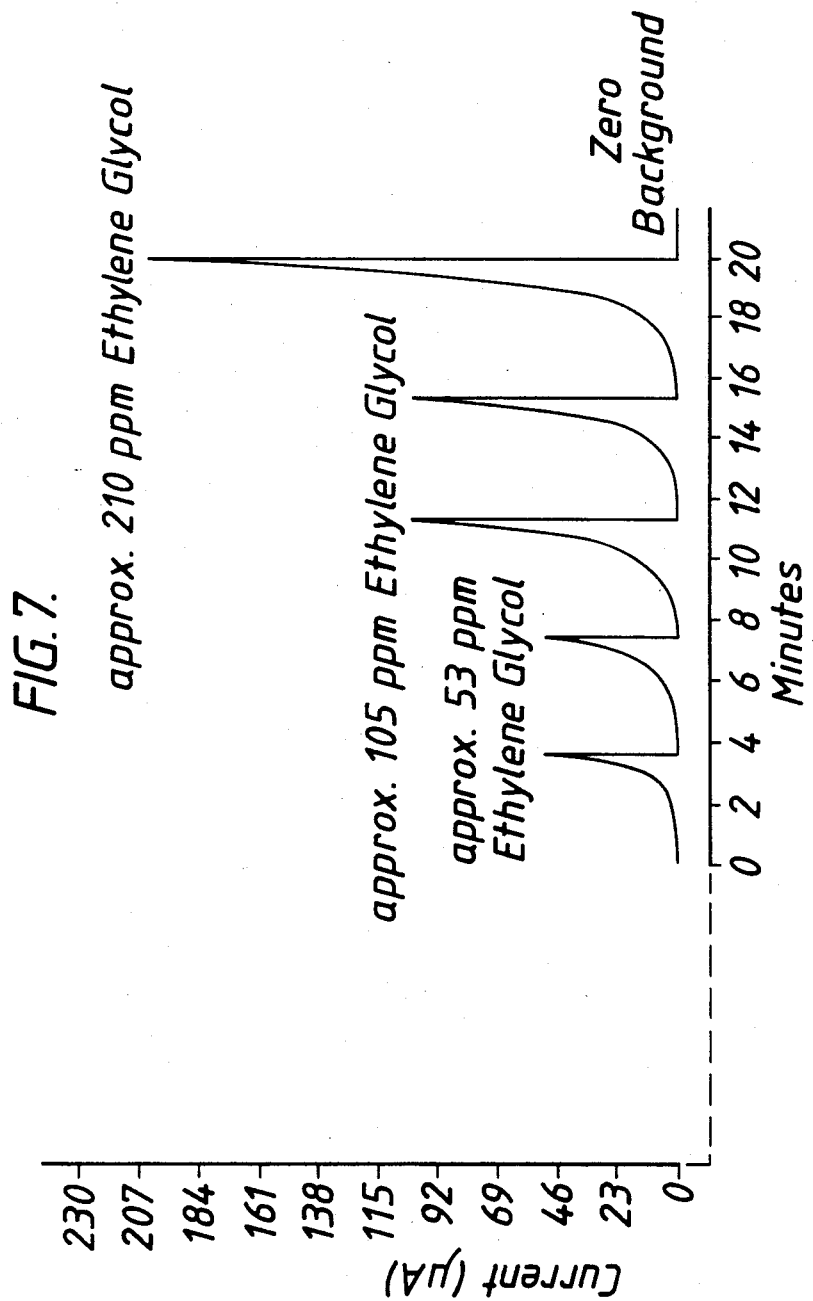

GAS SENSOR AND METHOD

This application is a continuation of Ser. No. 814,168 filed Dec. 23, 1985 which in turn was a continuation of Ser. No. 724,037 filed Apr. 17, 1985 which in turn was a continuation of Ser. No. 603,933 filed Apr. 26, 1984 and all now abandoned.

This invention relates to the detection of gases and more particularly to methods and apparatus for detecting and measuring water soluble gases.

Water soluble gases, such as ammonia, can be detected and measured by an electrochemical technique known as polarography. Potential difference changes are indicative of both the presence and concentration of solute in the electrolyte.

Hitherto 'capillary type systems' have been used, as in fuel cells, in which the gas phase is presented to an interface between an electrolyte and the electro-active working electrode via capillary like cylindrical pores. A disadvantage of this technique is that the gas-electrolyte interchange is rather slow and the gas saturated electrolyte has to travel a not inconsiderable distance between gas phase itself and the electrode working surface via the electrolyte contained in the pores. Thus the speed of response is relatively poor. The walls of the material are treated or made of material which is hydrophobic to retain the electrolyte and prevent floating through or within the pores.

We have now found that the response time can be accelerated and that gas concentrations over a large range can be determined employing an electrode system whereby the three phases, gas, electrolyte and electro-active substrate come into very close proximity.

In accordance with this invention there is provided an electrochemical cell for use in the detection and measurement of water soluble gases including a vessel having a first chamber adapted to receive and contain said gas and having located therein a working electrode and a second chamber adapted to contain an electrolyte and having located therein a reference electrode arranged to be in contact with said electrolyte, there also being located within said vessel a counter electrode, wherein said working electrode consists of an absorbent material communicating between said first and second chambers, which is adapted to be in contact with said electrolyte and has an electro-active substrate sputtered on at least a portion of the surface of that part of the material located in the first chamber.

The present invention also provides apparatus for the detection and measurement of water soluble gases including an electrochemical cell as defined above, means for delivering a quantity of gas into said first chamber means for supplying an electric current between said working and counter electrodes thereby to effect an electrochemical reaction and means for measuring changes in current proportional to the quantity or concentration of the gas undergoing reaction occuring at the reference electrode upon supply of said electric current.

The invention further provides a method for detecting and measuring the concentration of a water soluble gas which comprises subjecting said gas to an electrolytic reaction in an electrochemical cell as defined above and expressing concentration of said gas as a function of measured potential difference between the electrodes when said electrolytic reaction is taking place.

According to one embodiment of the invention, the counter electrode is located, together with the working electrode, in the first chamber. Alternatively, the counter electrode may be located in the second chamber; this being preferred if the electrical resistance of the electrolyte is low, say less than 1 Kohm.

The 'absorbent material' may be a fibrous material and can be natural cellular material, or preferably is a synthetic polymeric material, which is rolled to give the texture and appearance of coarse paper. The nominal thickness of this open-laminar material may range from 0.15 to 0.2 mm whilst the thickness of the individual fibres may range from 0.008 to 0.01 mm.

The material should possess sufficient heat resistance for it to maintain its integrity during the metal sputtering process.

The invention will be further described with reference to the accompanying drawings in which:

FIG. 4 is a sectional representation of an electrode assembly; and

FIGS. 5, 6 and 7 are graphs.

Figure 1:
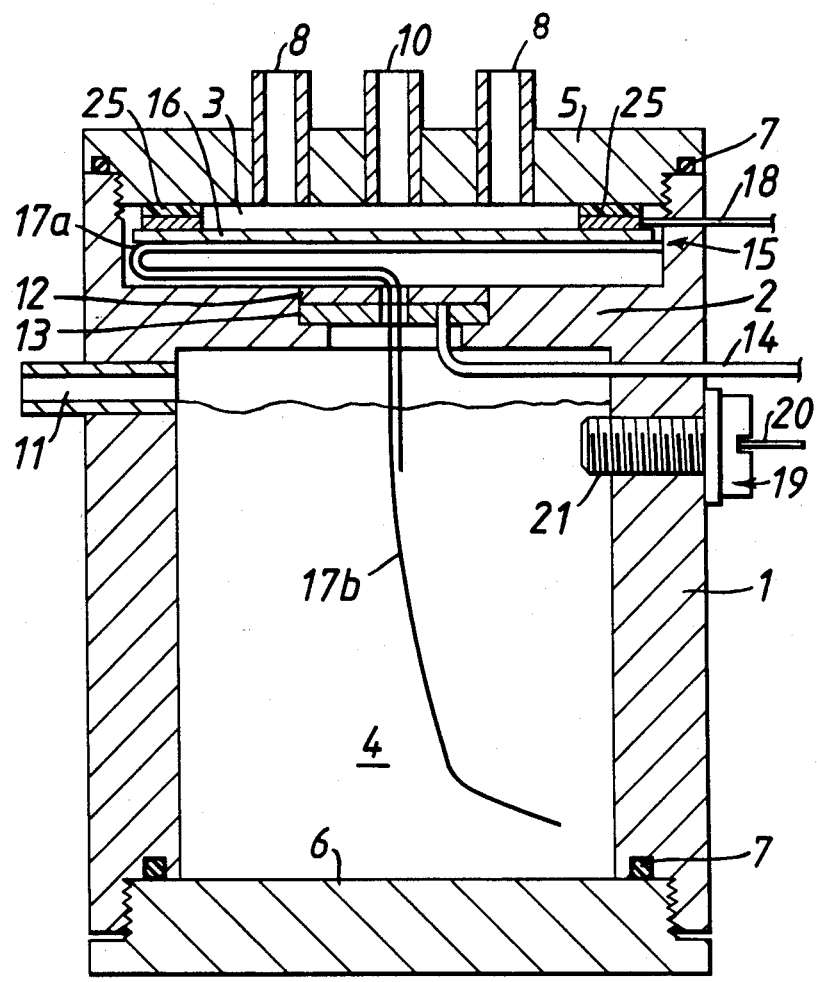
FIG. 1 is an elevational view in section of an electrochemical cell in accordance with the invention.

Referring to FIG. 1, the electrochemical cell body 1 is a cylindrical shaped vessel divided into two regions by a septum 2. The upper region or chamber 3 is the gas sample chamber and the lower region or chamber 4 is the electrolyte chamber. Each of the chambers is closed off by end plates 5 and 6 respectively which are threaded so as to co-operate with the corresponding threads cut on the inner surface of body 1. In order to provide a fluid tight seal O-rings 7 are provided.

End plate 5 is provided with gas inlet and outlet ports 8 and an electrolyte inlet port 10. An electrolyte outlet port 11 is provided in the side of the body 1.

Septum 2 is axially bored and counter-bored to provide a shouldered location for the counter electrode 12 and a supporting disc 13.

The connecting wire 14 for the counter electrode is led through the cell body by a suitable drilled and sealed hole.

In an alternative embodiment (not shown), the counter electrode may be mounted on the base plate 6, the necessary electrical connections being made through the plate.

Within the gas sample chamber 2 is mounted the working electrode generally denoted 15. This electrode comprises a fibrous metallised mat 16 in intimate physical contact with a second piece of non-metallised fibrous mat 17a, the tails 17b of which extend through an axially bored hole or slot in the counter electrode/support assembly 12, 13 into the electrolyte chamber 4. The working electrode 15 is mounted in chamber 3 in such a manner that it is not in electrical contact with the reference electrode. A wiring connection 18 for the working electrode is provided through the side of body 1.

A reference electrode 19 is mounted in the lower electrolyte chamber 4 and is provided with an electrical contact wire 20.

The materials for the reference electrode will depend upon the electrochemical reading under investigation. For example, a mercurous oxide reference would be used for gases much as ammonia, and oxygen whilst for chloride or hydrogen a mercurous sulphite reference electrode would be used. The following is a method for the typical preparation of a mercurous oxide reference electrode; for a mercurous sulphate electrode, sulphuric acid would be used instead of the potash.

The reference electrode 19 may be built as a complete unit with the reference electrode housed in a hollow nylon screw 21 and may be constructed as illustrated in FIG. 4. A platinum spade 22 is spot welded to a piece of platinum wire 20 then cleaned in hot aqua rega and boiling distilled water before being washed in 1.0M potassium hydroxide. The spade is next electrochemically amalgamated using mercury covered in a layer of 1.0M KOH. The spade to be amalgamated is made the cathode and a second platinum spade the anode. The anode is immersed in the KOH layer and then the cathode is slowly introduced, with a potential of 3 volts being applied, and gas evolution should be seen. After letting the gas evolve for a few seconds the spade is quickly dipped into the mercury layer to amalgamate it. The amalgamated spade is next coated with a mercurous oxide skin. This is accomplished by keeping mercury in contact with fine mercurous oxide powder in order to produce a mercurous oxide layer on the external surface of the mercury. This layer is then lifted off using the freshly amalgamated spade. The spade is potted into the nylon screw and left overnight. A porous PTFE sinter 23 is cut to fit the end of the screw and saturated with 1.0M KOH.

The hollow compartment 24 is filled completely with 1.0M KOH and the PTFE plug 23 inserted. The potential of the Hg/HgO reference should be in the region of $-122$ mv when compared with a calomel and 370 mr for the mercurous sulphate reference in 1M sulphuric acid. The completed electrode is stored in 1.0M KOH until required.

The counter electrode 12 may be cut from a piece of lead foil and cleaned using emery paper. A slot is cut to receive the tail from the blank matting and working electrode to maintain electrical contact with the electrolyte. To one side of the counter is soldered the wire contact which is sealed, with, for example an epoxy based resin, to protect it from the electrolyte and allowed to dry. The foil may be affixed to a similar support 13 to give the system rigidity. Finally, the resistance across the foil and wire is checked and should be less than 1 ohm.

A circular piece of matting 17a is cut to size with an extended tail piece 17b to use as a blank in order to prevent shortening between the working and counter electrode when assembly is complete. If the counter is fixed in the base, foil or lead wire may be used and fitted via a hole drilled in the base plate and sealed with, for example, an epoxy based adhesive.

The working electrode 15 and contact 18 is made up from a piece of matting cut to the same shape as the blank and the circular portion sputtered with an electro active material, e.g. gold. The tail piece is kept protected whilst being sputtered to prevent gold deposition. A layer of metal (e.g. gold) corresponding to 4,000 angstrom units may be applied and the resistance across it checked, less than 5 ohms is considered satisfactory. The gold/PTFE contact is assembled by sputtering a layer of gold, 4,000 angstrom units, onto a PTFE former. A gold wire contact is inserted into the PTFE and a further layer of gold sputtered to ensure electrical contact, (less than 5 ohms resistance). Other metals where appropriate may be used, e.g. Pt, Pd and other transitional metals or their alloys.

After the individual components have been constructed they are assembled into the body 1. Assembly starts at the top of the sensor with the two end plates 5, 6 removed. The counter/support 12, 13 is fitted into the shouldered recess of septum 2 and the wire contact passed through a hole in the sensor wall. The working electrode 15 and blank matting 17a are inserted together, with the tail pieces 17b passing through the slot in the counter 12, 13. The mattings are bedded down so they are flat and the working electrode does not short with the counter electrode. The slack in the tails may be taken out by pulling them gently through the slot. The gold/PTFE contact 18 is then carefully lowered onto the sputtered matting with the gold wire contact passing through the hole in the sensor wall and a PTFE former 25 is inserted to protect the contact when tightening up the top plate 5. The top plate is fitted and slowly tightened up in order not to damage the gold contact. The reference 19 is now screwed into the side of the sensor and the bottom plate 6 plus 'O' ring 7 inserted. Care must be taken when tightening the bottom plate to ensure the matting is not caught. The receiving holes for the wire contacts are sealed using sealant and left to cure. The sensor is filled with electrolyte, (e.g. 1.0M KOH) using a syringe through port 10 until it starts to drain from port 11 in the side of the body. The sensor is now assembled and ready for operation in conjunction with a potentiostat (see FIG. 2).

The unique construction of the working electrode in the cells of the invention, allowed the three phases, gas, electrolyte and electro active substrate to come into very close proximity and thus overcomes the disadvantages of known membrane/capilliary systems in which gas-electrolyte interchange is rather slow and the gas saturated electrolyte has to travel to an electro-active working electrode some distance away from the gas phase. With the electrode system of the present invention electrolyte is drawn through the matting by capillary action due to the loose weave and semi-absorbent nature of the material and forms a very thin film of electrolyte on the electro-active substrate and is in direct contact with the gas under analysis.

Figure 2:
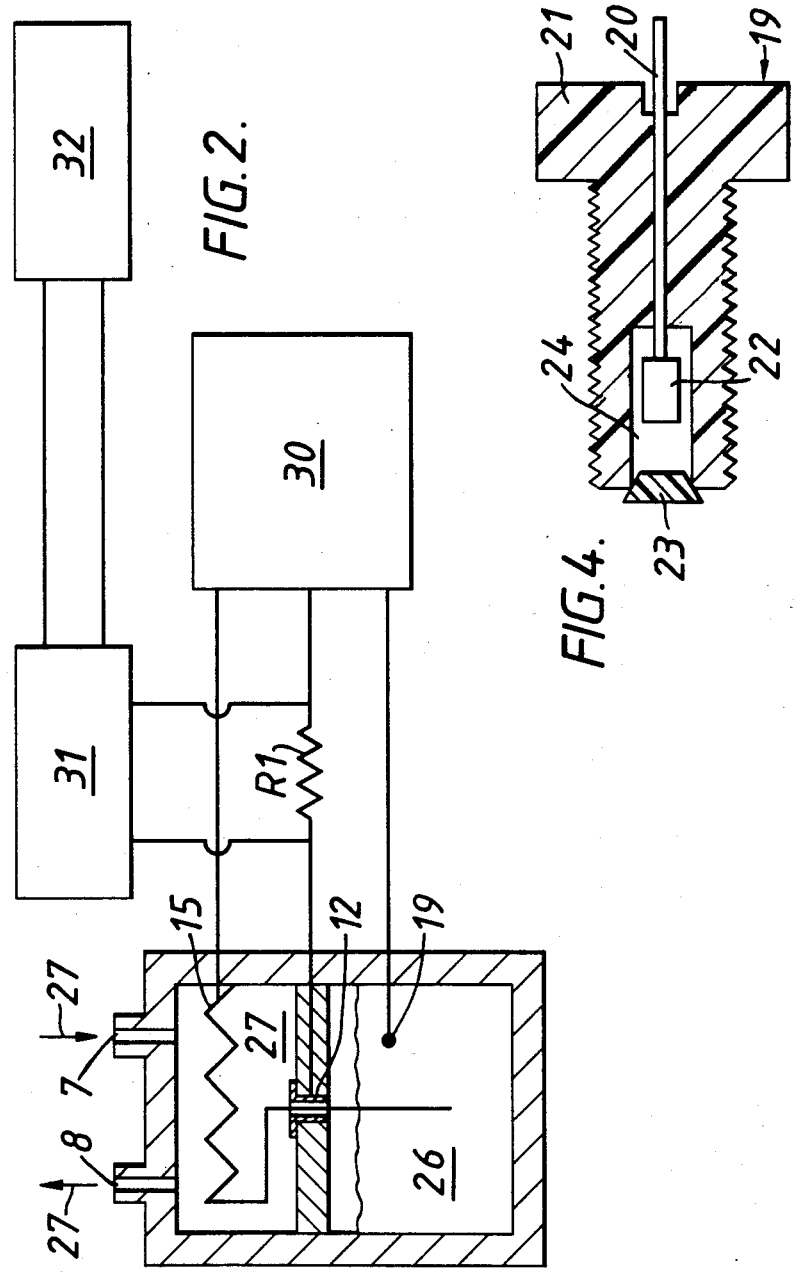
FIG. 2 is a schematic block diagram of apparatus in accordance with the invention.

Referring to FIG. 2, the lower chamber 4 is filled with a suitable electrolyte 26. The three electrodes 12, 15 and 19 are immersed in or contacted with electrolyte 26.

The potential of the working electrode 15 is held constant with respect to the reference electrode 12 via a potentiostat 30 in a region where the reacting gas to be measured is electrochemically oxidised eg ammonia or reduced eg oxygen at the working electrode. The potential range chosen for operation is sufficiently restricted to confer a high degree of specifity, i.e. to avoid cross sensitivity to any other components which may be present in the carrier gas 27. If the gas is oxidised at the working electrode a reduction occurs at the counter electrode and vice-versa. The current generated by the electrochemical reaction is measured as the potential drop across a current measuring resistor R1 which is mounted in series with the counter electrode. Polarographic cells are operated in the diffusion limited mode which means the rate of reaction is limited by the rate of diffusion of reacting gas to the working electrode. Under this operation mode the current output from the sensor is directly proportional to the concentration (partial pressure) of reacting gas in the gas sample. Zero back off facilities and amplification are also provided by circuit 31. The output signal from the sensor can them be followed using a chart recorder 32 or the concentration read off directly in ppm using a calibrated digital display.

Figure 3:
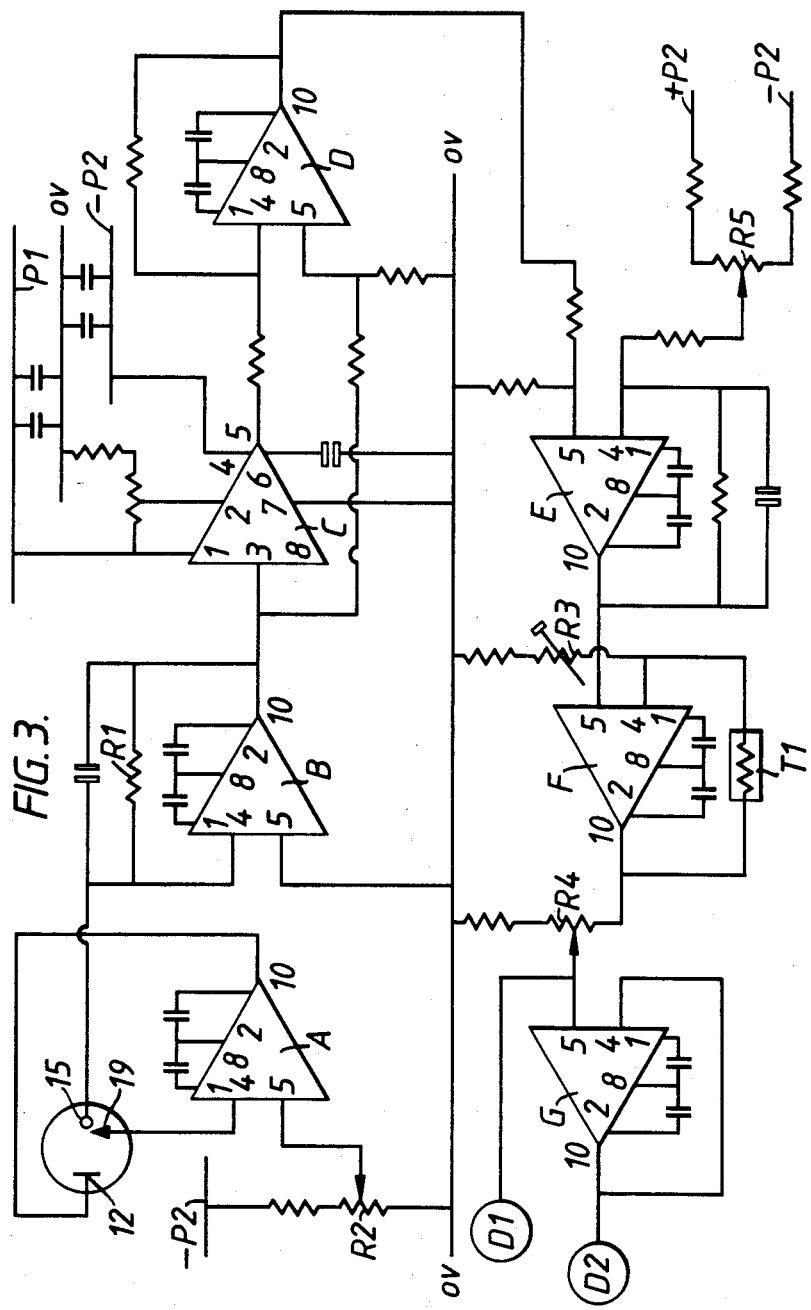
FIG. 3 is a circuit diagram of a typical embodiment of the analogue circuitry.

FIG. 3 is a circuit diagram for processing the analogue signal information received for the electrochemical cell, and encompasses both elements 30 and 31 (FIG. 2).

The circuitry is sub-divided into six elements each having a specific function. Power is supplied to the circuit by two power rails P1 and P2 which respectively provide current to drive the operational amplifiers and to provide a lower voltage for zeroing and maintaining fixed positive potentials. Typically the voltages applied at P1 and P2 are of the order of 6.5 V to drive 7605 chopper stabilised operational amplifiers and about 1.26 V to offset background of the sensor 19 and to supply a fixed positive potential e.g. +500 mV to sensor 19 via manual zero R2.

The potentiostat 30 is provided by the circuitry associated with the operational amplifiers A and B. Current is supplied to electrode 15 and the potential difference of 15 with respect to 19 is reassured across the current reasuring resistor R1. Output from the potentiometer is fed to Auto-zero circuit (C and D).

The auto-zero circuitry is used to negate any background drift of the sensor prior to a sampling run. The auto zero is controlled via rheostat R3 and has 2 operational modes, zero and run. The circuit consists of monolithic sample and hold chip (C) and an operational amplifier (D) in a differential configuration. When in the zero mode the sample and hold chip is constantly sampling the output from the potentiostat—which is also fed directly to the operational amplifier D. (Voltage+P1 being applied to the logic input). Hence when the sample and hold chip is sampling, the 2 inputs to the differential amplifier are the same, therefore the output reads zero. The auto zero is brought into operation by applying 0V to the logic input. This causes the sample and hold chip to hold background value which is then applied to one of the inputs of the operational amplifier D.

Thus if there is change in the signal from the potentiostat the difference is given as the output from D.

Any background signal may be offset manually by variation of R5. Again, a differential operation amplifier configuration (E) is used. The input signal is offset by applying a potential (from the P2 voltage rail) of equal potential to the 2nd input and hence a zero output is obtained.

Temperature compensation is controlled through the coupled thermistor T1-operational amplfier F system to give a gain of 4.

Calibration is accomplished by adjusting a variable resistor R4 which provides an input to the digital display D1 which is proportional to concentration, thus enabling a direct read-off from the display.

A unit gain amplifier 6 is also provided which prevents the current drain from a chart recorder D2 from interfering with the signal to the digital display.

The apparatus is intended for both laboratory and field use and therefore may be supplied with battery power or by a suitable stabilised and rectified mains supply. For battery powered operation the apparatus may include means and circuitry for re-charging the service batteries.

The apparatus of the invention is suitable for the detection and measurement of gases and vapours which are water soluble, i.e. soluble in the electrolyte.

The invention can be employed for the detection of ammonia or carbon dioxide in air using Pb-KOH-Au systems or for the detection of polar organic species such as monoethylene glycol in methane contacting gas mixtures such as natural or substitute natural gas using Pt/Au electrode systems with hydrochloric acid as the electrolyte, in which the glycol is oxidised through to carbon dioxide and water.

FIG. 5 is a graph showning changes in current (as measured across R1) with changes in the concentration of ammonia. The speed of response is less than 5 seconds and although these results show a slight exponential tendency over the total range 10–1000 ppm, the approach to linearity in the range 10–100 ppm is very good.

FIG. 6 shows that for ethylene glycol applications the response is linear over the range 0–250 ppm.

FIG. 7 is a graph illustrating the response and recovery time for the various concentrations of MEG sampled serially in apparatus according to the invention. From those results it can be seen that the speed of response is almost instantaneous and that the recovery time between samples is less than 5 minutes.

I claim:

1. An electrochemical cell for use in the detection and measurement of water soluble gases including a vessel having a first chamber adapted to receive and contain said gas and having located therein a working electrode and a second chamber adapted to contain an electrolyte and having located therein a reference electrode arranged to be in contact with said electrolyte, there also being located within said vessel a counter electrode, said vessel further comprising a length of material capable of absorbing electrolyte, a part of said material extending between said first and second chambers and being adapted to be in contact with said electrolyte, and said working electrode comprising a metal layer substrate sputtered on at least a portion of the surface of that part of the material which is located in the first chamber.

2. Apparatus for the detection and measurement of water soluble gases including an electrochemical cell comprising a vessel having a first chamber for receiving and containing such gases and having located therein a working electrode and a second chamber for receiving and containing an electrolyte and having located therein a reference electrode arranged to be in contact with said electrolyte, said vessel further including a counter electrode located therein and a length of a material located therein which is capable of absorbing electrolyte, a portion of said material extending between said first and second chambers and being adapted to be in contact with said electrolyte, and said working electrode comprising a metal layer substrate sputtered on at least a part of the surfaces of that portion of the material which is located in the first chamber, said apparatus further comprising means for delivering a quantity of gas into said first chamber, means for supplying an electric current between said working and counter electrodes thereby to effect an electrochemical reaction and means for measuring changes in current proportional to the quantity or concentration of the gas undergoing reaction occuring at the reference electrode upon supply of said electric current.

3. A method for detecting and measuring the concentration of a water soluble gas which comprises subjecting said gas to an electrolytic reaction in an electrochemical cell comprising a vessel having a first chamber for receiving and containing said gases and having located therein a working electrode and a second chamber for receiving and containing an electrolyte and having located therein a reference electrode arranged to be in contact with said electrolyte, said vessel further including a counter electrode located therein and a length of material located therein which is capable of absorbing electrolyte, a portion of said material extending between said first and second chambers and being adapted to be in contact with said electrolyte, and said working electrode comprising a metal layer substrate sputtered on at least a part of the surface of that portion of the material which is located in the first chamber, and said method further comprising expressing concentration of said gas as a function of measured potential difference between the electrodes when said electrolyte reaction is taking place.

* * * * *